United States Patent [19]

Goddard

[11] 4,138,242
[45] Feb. 6, 1979

[54] NOVEL 2-ARYL-2,3,5,6,7,8-HEXAHYDRO-3-THIOX-OIMIDAZO-[1,5-A-]PYRIDIN-1(8AH)-ONES AS HERBICIDES

[75] Inventor: Steven J. Goddard, West Grove, Pa.

[73] Assignee: E. I. Du Pont de Nemours and Company, Wilmington, Del.

[21] Appl. No.: 748,297

[22] Filed: Dec. 7, 1976

Related U.S. Application Data

[63] Continuation of Ser. No. 667,535, Mar. 17, 1976, abandoned, which is a continuation-in-part of Ser. No. 546,698, Feb. 3, 1975, Pat. No. 3,958,976.

[51] Int. Cl.$^2$ .................. A01N 9/22; C07D 471/04
[52] U.S. Cl. .................................. 71/92; 546/121; 546/226
[58] Field of Search .................. 260/293.55; 71/92

[56] References Cited

FOREIGN PATENT DOCUMENTS 1445797  3/1969  Fed. Rep. of Germany.
1114397  5/1968  United Kingdom.

OTHER PUBLICATIONS

Stanovnik et al., Croatica Chem. Acta, 35, 167–170, (1963).
C. A., 62, (1965), 16258, G. E.
Fifth Asian–Pacific Weed Science Society Conference, Oct. 5–11, 1975 16 page report.
Winterfeld et al., Arch. Pharm., 293, 203–210, (1960).

*Primary Examiner*—Joseph Paul Brust

[57] ABSTRACT

This invention relates to novel 2-aryl-2,3,5,6,7,8-hexahydro-3-thioxoimidazo[1,5-a]pyridin-1(8aH)-ones and their use as herbicides. These novel compounds may be used for selective weed control in certain crops or for total vegetation control.

2 Claims, No Drawings

NOVEL 2-ARYL-2,3,5,6,7,8-HEXAHYDRO-3-THIOX-OIMIDAZO-[1,5-A-]PYRIDIN-1(BAH)-ONES AS HERBICIDES

RELATED APPLICATION

This application is a continuation of my copending application U.S. Ser. No. 667,535, filed Mar. 17, 1976, now abandoned, which is in turn a continuation-in-part of my application U.S. Ser. No. 546,698 filed Feb. 3, 1975, now U.S. Pat. No. 3,958,976, issued May 25, 1976.

BACKGROUND OF THE INVENTION

A number of isoindole-type compounds are known in the prior art. Recently, in German Offenlegungsschrift No. 2,165,651 a group of isoindole-1,3-diones which are useful as herbicides was disclosed. The general formula for the isoindole-1,3-diones is as follows:

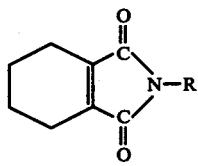

wherein R may be aryl, aralkyl or benzyl optionally substituted with 1 to 5 halogen atoms, hydroxy, nitro, cyano, thiocyano, carboxy, alkyl or halogerated alkyl, lower alkoxy or alkylthio, or phenyl groupings; a group having the configuration —O—CH$_2$A may also be substituted therein, wherein A is a phenyl or a naphthyl group, wherein the phenyl group may have one or more substitutions therein, such as halogen atoms, nitro groupings, lower alkyl groupings or lower alkoxy groupings.

Typical of the compounds disclosed in the Offenlegungsschrift is the compound:

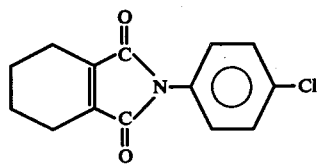

Although herbicides such as the herbicide discussed above have proven effective for controlling undesired vegetation, there is a constant need for improved herbicides because of the current critical food shortages in the world. Any improvement in herbicidal activity, in conjunction with no significant damage to the crop which is to be protected, is significant. Consequently, it is readily apparent, that there is a continuing need for improved herbicides.

According to the instant invention a novel improved herbicide has been discovered.

SUMMARY OF THE INVENTION

This invention relates to the novel compounds of Formula I, to compositions containing them and to their use as herbicides

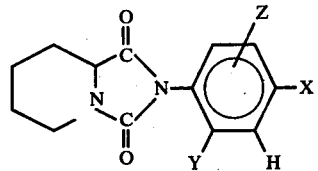

Formula I wherein
Z is hydrogen or fluorine;
Y is hydrogen or fluorine; and
X is bromine, chlorine, fluorine, methoxy, cyano or nitro; provided that when Z is in the meta position and is fluorine, Y must also be fluorine.

It is most preferred for economic reasons and/or greater herbicidal activity that X is Cl and Y and Z are H.

This invention also includes herbicidal compositions containing the above compounds as active ingredients and methods of controlling undesirable vegetation by applying the compounds and/or compositions to the locus of such undesired vegetation.

DESCRIPTION OF THE INVENTION

This invention relates to the novel compounds of Formula I, to compositions containing them and to their use as herbicides

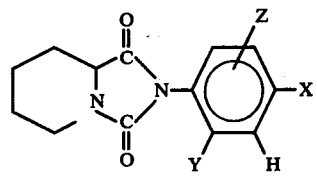

Formula I wherein
Z is hydrogen or fluorine;
Y is hydrogen or fluorine; and
X is bromine, chlorine, fluorine, methoxy, cyano, or nitro; provided that when Z is in the meta position and is fluorine, Y must also be fluorine.

PREFERRED COMPOUNDS

Preferred for economic reasons and/or for their greater herbicidal activity are the compounds of Formula I wherein
Z is hydrogen or fluorine;
Y is hydrogen or fluorine: and
X is chlorine or fluorine provided that (1) when X is fluorine at least one of Y or Z must be fluorine, (2) when X is chlorine, at least one of Y or Z must be hydrogen, and (3) when Y and Z are both fluorine, X is also fluorine.

The most preferred compound of the instant invention for economic reasons is:
2-(4-chlorophenyl)-2,3,5,6,7,8-hexahydro-3-thioxoimidazo[1,5-a]pyridin-1(8aH)-one

SYNTHESIS OF THE COMPOUNDS

The novel compounds of Formula I can be prepared as shown in the following reaction sequence:

General Reactions

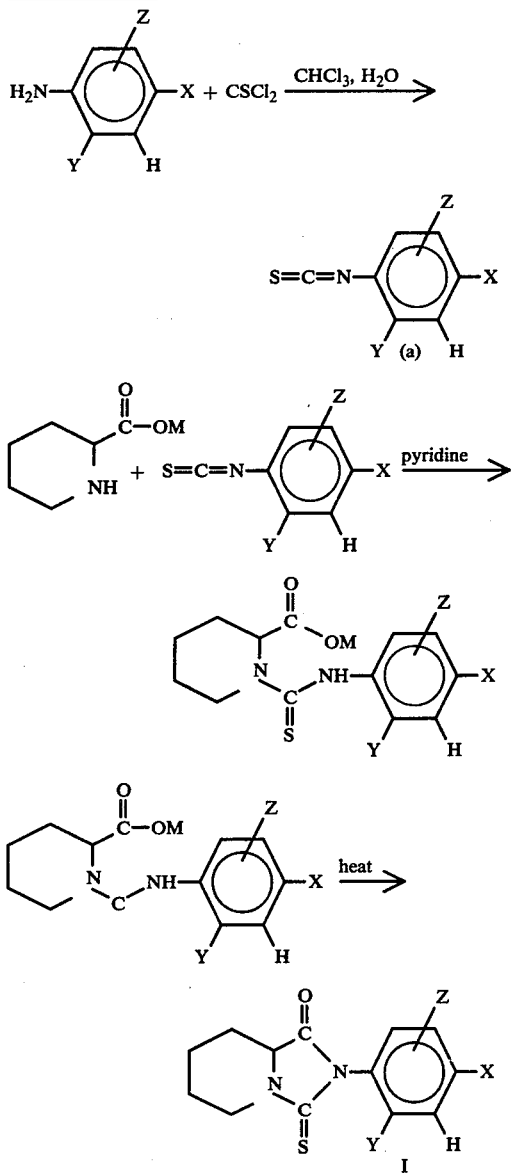

wherein
M is Na, K or Li, and X, Y, and Z are as defined above.

STEP 1

The preparation of aromatic isothiocyanates from anilines is well known to those skilled in the art. For example, the method of J. E. Hodgkins and W. P. Reves [J. Org. Chem., 29, 3098 (1964)] can be used. Alternatively, an aniline can be treated with thiophosgene in chloroformwater mixtures over several hours (i.e. 2 to 20) at 0° C. to ambient temperature.

STEP 2 AND 3

The 2-aryl-2,3,5,6,7,8-hexahydro-3-thioxoimidazo[1,5-a]pyridin-1(8aH)-ones can be prepared by the methods of K. Winterfield and H. Schula [Arch. Pharm., 293, 203 (1960)] and W. D. Marshall, et. al. [Can. J. Chem., 53, 41 (1975)].

An aromatic isothiocyanate of formula (a) is added dropwise, at ambient temperature and pressure, to a solution of 2-piperidinecarboxylic acid in pyridine and aqueous base (i.e. 10% sodium carbonate).

Upon heating to 60°–80° on a steam bath for several hours (i.e. 3–10), the 1-arylaminothiocarbonyl-2-piperidinecarboxylate salt is cyclized to a 2-aryl-2,3,5,6,7,8-hexahydro 3-thioxoimidazo[1,5-a]pyridin-1(8aH)-one. The product is isolated by pouring the reaction mixture over ice and extracting with a water-immiscible solvent (i.e., chloroform). The organic extract is washed with an aqueous solution of a mineral acid (such as hydrochloric acid), dried over a dessicant (such as anhydrous sodium sulfate) and stripped of solvent under reduced pressures (i.e. 100–300 mm.Hg). If needed, a purification can be effected by chromatography on silica gel using a 1:1 mixture of hexane and benzene.

Certain of the anilines employed in the synthesis of the compounds of this invention are novel. 4-Chloro-2-fluoroaniline, for example, can be prepared from 2′-fluoroacetanilide [G. Schiemann and H. G. Baumgarten, Chem. Berichte 70, 1416 (1937)] by the reaction sequences shown below.

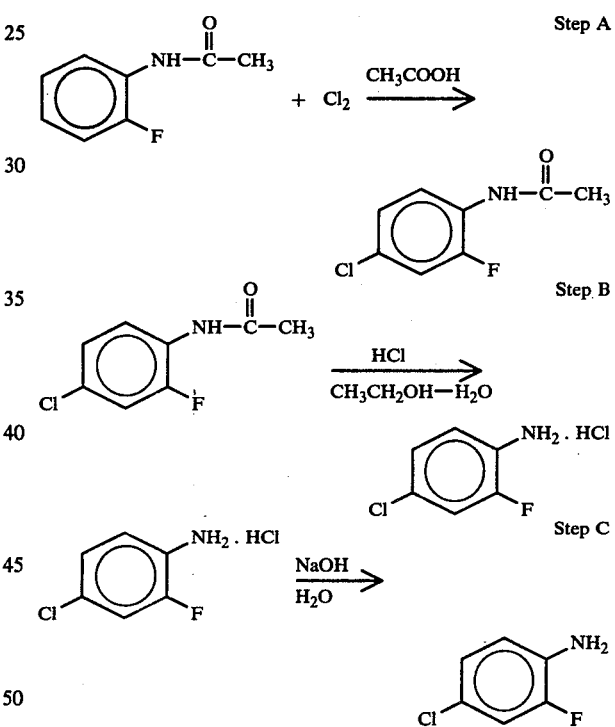

STEP A

The chlorination of acetanilides in acetic acid is well known to those skilled in the art, and may be carried out under the conditions taught in W. W. Reed and K. J. P. Orton, J. Chem. Soc., 91, 1543 (1907) for the chlorination of acetanilide. The chlorination of 2′-fluoroacetanilide takes place at 25°–30° C. over several hours (e.g. 5) at atmospheric pressure. The resulting product is 4′-chloro2′-fluoroacetanilide.

STEP B

4′-Chloro-2′-fluoroacetanilide is refluxed in a mixture of a lower alcohol (50%) (e.g. ethanol) and concentrated hydrochloric acid (50%) for several hours (e.g. 5 or more) at 70°–90° C. and atmospheric pressure. The solvent mixture is removed at a reduced pressure of 100 to 300 mm.Hg and 20°–50° C. to leave a residue of the hydrochloride salt of 4-chloro-2-fluoroaniline.

STEP C

After basification of an aqueous solution of the hydrochloride salt of 4-chloro-2-fluoroaniline with an alkali metal hydroxide solution such as 50% sodium hydroxide at ambient conditions, the free 4-chloro-2-fluoroaniline is extracted into a suitable water-immiscible organic solvent such as ethyl ether or methylene chloride. The crude 4-chloro-2-fluoroaniline is isolated by removal of the organic solvent under reduced pressure of 100 to 300 mm.Hg at 20°–50° C.

2-Fluoro-4-bromoaniline can be prepared by bromination of 2-fluoroaniline [prepared in Chem. Berichte, 70, 1416 (1937)] with N-bromosuccinimide as shown in the following equation.

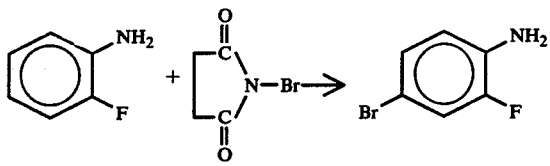

The bromination of anilines using N-bromosuccinimide in an inert organic solvent such as methylene chloride is well known to those skilled in the art, e.g., J. B. Wommack et. al., J. Het. Chem., 6, 243 (1969). The bromination of 2-fluoroaniline is an exothermic reaction that takes place at 0° C. over several hours, e.g. 5 or more. The resulting reaction mixture is washed with water several times and dried with an appropriate drying agent such as anhydrous sodium sulfate. The 4-bromo-2-fluoroaniline is recovered by removal of the organic solvent under reduced pressure of 100 to 300 mm.Hg at 20°–50° C.

2,4,6-Trifluoroaniline is prepared by reduction of 1,3,5-trifluoro-2-nitrobenzene [V. I. Siele and H. J. Matsuguma, U.S. Dept. Com., Office Serv., P B Rept. 145, 510, p. 1 (1960) or Chem. Abstr., 56, 15394c (1962)] using the procedures described by G. Schiemann and M. Seyhan, Chem. Berichte, 70, 2396 (1937).

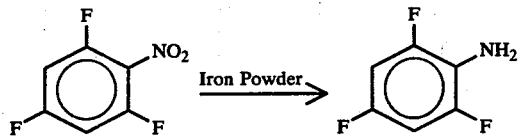

2,4-Difluoroaniline is known to the art and can be prepared by the procedure described in G. Schiemann and M. Seyhan, Chem. Berichte, 70, 2396 (1937).

The following examples further illustrate the method for synthesis of compounds of this invention. All parts are by weight and all temperatures in degrees centigrade unless otherwise indicated.

EXAMPLE 1

Preparation of 4-Chloro-2-fluoroaniline

Seventy-one parts of liquid chlorine were added to a solution of 140 parts of 2'-fluoroacetanilide in 500 parts glacial acetic acid, during one hour, at 25°–27°, with ice-water cooling. While stirring for 4 hours at 25°–27°, 4'-chloro-2'-fluoroacetanilide precipitated. After collecting the product by filtration, the filtrate was poured over 2000 parts of ice. The resulting second portion of precipitated product was collected by filtration, combined with the first portion and recrystallized from 700 parts of methanol at −45° to yield 119 parts of 4'-chloro-2'-fluoroacetanilide as white crystals melting at 152°–155°.

A mixture of 119 parts of 4'-chloro-2'-fluoroacetanilide in 475 parts of ethanol and 200 parts of 37% hydrochloric acid was refluxed for 17 hours and the solvent removed under a reduced pressure of 300 mm.Hg to yield the moist, solid hydrochloride salt of 4-chloro-2-fluoroaniline.

The moist, solid hydrochloride salt of 4-chloro2-fluoroaniline was cooled to 10° in an ice-acetone bath and 50% aqueous sodium hydroxide was added dropwise, with stirring, until pH 11 was obtained. The resulting two-phase mixture was extracted four times; 500 parts of methylene chloride were used for each extraction. The combined organic extracts were dried with anhydrous sodium sulfate and the solvent removed under reduced pressure of 300 mm. Hg to leave 89 parts of light brown, oily 4-chloro-2-fluoroaniline, $n_D^{25} = 1.5541$.

EXAMPLE 2

Preparation of 4-Bromo-2-fluoroaniline

160 Parts of solid N-bromosuccinimide were added in portions over a 2-hour period to a solution of 100 parts of 2-fluoroaniline in 400 parts of methylene chloride cooled to 0°. After stirring for 20 minutes, the dark red mixture was washed four times; 200 parts of cold water were used for each washing. The red organic phase was dried with anhydrous sodium sulfate and evaporated under 300 mm.Hg to 164 parts of brown, oily 4-bromo-2-fluoroaniline, $n_D^{25}$: 1.5885.

EXAMPLE 3

Preparation of 4-Chloro-2-fluorophenyl Isothiocyanate

To a mixture of 75 parts of chloroform and 100 parts of ice and 15 parts of 4-chloro-2-fluoroaniline, 14.2 parts of thiophosgene were added dropwise over 15 min. After allowing the warm to room temperature and stirring overnight, the phases were separated. The aqueous phase was extracted with 50 parts of chloroform. The organic phases were combined, dried with anhydrous sodium sulfate and evaporated at 300 mm.Hg and 25° to yield 21.3 parts of 4-chlorophenyl-2-fluorophenyl isothiocyanate as a yellow oil with a $n_D^{25}$ of 1.6343.

The following isothiocyanates can be prepared by substituting the appropriately-substituted aniline for 4-chloro-2-fluoroaniline in Example 3:
4-bromo-2-fluorophenyl isothiocyanate
4-methoxyphenyl isothiocyanate
2,4,6-trifluorophenyl isothiocyanate
2,4-difluorophenyl isothiocyanate
4-chlorophenyl isothiocyanate
4-bromophenyl isothiocyanate
4-fluorophenyl isothiocyanate
2-fluoro-4-methoxyphenyl isothiocyanate
4-chloro-2,5-difluorophenyl isothiocyanate
4-chloro-2,6-difluorophenyl isothiocyanate
4-cyano-2-fluorophenyl isothiocyanate
4-cyano-2,5-difluorophenyl isothiocyanate
2,5-difluoro-4-nitrophenyl isothiocyanate
2,5-difluoro-4-methoxyphenyl isothiocyanate

EXAMPLE 4

Preparation of
2-(4-Chloro-2-fluorophenyl)-2,3,5,6,7,8-hexahydro-3-thioxoimidazo[1,5-a]pyridin-1(8aH)-one To a solution of 12.9 parts of piperolinic acid in 100 parts of pyridine and 50 parts of a 10% aqueous sodium carbonate, 21 parts of 4-chloro-2-fluorophenyl isothiocyanate was added dropwise over 10 min. After heating and stirring at 60° for 3 hr and stirring for 18 hours at ambient temperature. The reaction mixture was poured over a mixture of 2000 parts of ice, 500 parts of 37% aqueous hydrochloric acid and 400 parts of chloroform. The phases were separated and the aqueous portion washed with 300 parts chloroform. The combined chloroform extracts were washed with 200 parts of 10% aqueous hydrochloric acid, dried with anhydrous sodium sulfate and stripped at 25°, 300 mm Hg to yield a dark red glass. The crude product was chromatographed on 300 parts of Mallinckrodt SilicAR ® CC-7 special silica gel using 1:1 benzenehexane as the eluent. 10.3 Parts of 2-(4-chloro-2-fluorophenyl)-2,3,5,6,7,8-hexahydro-3-thioxoimidazo[1,5-a]pydridin-1(8aH)-one were obtained as an orange glass with $n_D^{25}$ of 1.6057.

The following compounds can be prepared by substituting the appropriately substituted aryl isothiocyanate for 4-chloro-2-fluorophenyl isothiocyanate in Example 4:

- 2-(4-bromo-2-fluorophenyl)-2,3,5,6,7,8-hexahydro3-thioxoimidazo[1,5-a]pydridin-1(8aH)-one
- 2-(4-methoxyphenyl)-2,3,5,6,7,8-hexahydro-3thioxoimidazo[1,5-a]pyridin-1(8aH)-one, m.p. 135°–136° C.
- 2-(2,4,6-trifluorophenyl)-2,3,5,6,7,8-hexahydro3-thioxoimidazo[1,5-a]pyriddin-1(8aH)-one
- 2-(2,4-difluorophenyl)-2,3,5,6,7,8-hexahydro-3thioxoimidazo[1,5-a]pyridin-1(8aH)-one
- 2-(4-chlorophenyl)-2,3,5,6,7,8-hexahydro-3-thioxoimidazo[1,5-a]pyridin-1(8aH)-one, m.p. 159°–160° C.
- 2-(4-bromophenyl)-2,3,5,6,7,8-hexahydro-3thioxoimidazo[1,5-a]pyridin-1(8aH)-one
- 2-(4-fluorophenyl)-2,3,5,6,7,8-hexahydro-3-thioxoimidazo[1,5-a]pyridin-1(8aH)-one
- 2-(2-fluoro-4-methoxyphenyl)-2,3,5,6,7,8-hexahydro-3-thioxoimidazo[1,5-a]pyridin-1(8aH)-one
- 2-(4-chloro-2,5-difluorophenyl)-2,3,5,6,7,8-hexahydro-3-thioxoimidazo[1,5-a]pyridin-1(8aH)-one, red glass
- 2(4-chloro-2,6-difluorophenyl)-2,3,5,6,7,8-hexahydro-3-thioxoimidazo[1,5-a]pyridin-1(8aH)-one
- 3-fluoro-4-(1,2,3,5,6,7,8,8a-octahydro-1-oxo-5-thioxoimidazo[1,5-a]pyridin-2-yl)benzonitrile
- 3,5-difluoro-4-(1,2,3,5,6,7,8,8a-octahydro-1-oxo3-thioxoimidazo[1,5-a]pyridin-2-yl)benzonitrile
- 2-(2,5-difluoro-4-nitrophenyl)-2,3,5,6,7,8-hexahydro-3-thioxoimidazo[1,5-a]pyridin-1(8aH)-one
- 2-(2,5-difluoro-4-methoxyphenyl)-2,3,5,6,7,8-hexahydro-3-thioxoimidazo[1,5-a]pyridin1(8aH)-one

FORMULATIONS OF THE COMPOUNDS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly,, contain about 1% to 99% by weight of active ingredient(s) and at least one of a) about 0.1% to 20% surfactant(s) and b) about 5% to 99% solid or liquid diluent(s). More specifically, they will contain these ingredients in the following approximate proportions:

|  | Percent by Weight | | |
|---|---|---|---|
|  | Active Ingredient | Diluent(s) | Surfactant(s) |
| Wettable Powders | 20–90 | 0–74 | 1–10 |
| Oil Suspensions, Emulsions, Solutions (including Emulsifiable Concentrates) | 5–50 | 40–95 | 0–15 |
| Aqueous Suspensions | 10–50 | 40–84 | 1–20 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et. al., "Handbook of Insecticide Dust Diluents and Carriers", 2nd Edn., Dorland Books, Caldwell, N.J. The more absorptive diluents are preferred for wettable powders and the denser ones for dusts. Typical liquid diluents and solvents are described in Marsden, "Solvents Guide", 2nd Edn., Interscience, New York, 1950. Solubility under 0.1% is preferred for suspension concentrates; solution concentrates are preferably stable against phase separation at 0° C. "McCutcheon's Detergents and Emulsifiers Annual", MC Publ. Corp., Ridgewood, New Jersey, as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff and "Perry's Chemical Engineer's Handbook", 4th Edn., McGraw-Hill, N.Y., 1963, pp. 8-59ff.

For further information regarding the art of formulation, see for example:

H. M. Loux, U.S. Pat. No. 3,235,361, Feb. 15, 1966, Col. 6, Line 16 through Col. 7, Line 19 and Examples 10 through 41.

R. W. Luckenbaugh, U.S. Pat. No. 3,309,192, March 14, 1967, Col. 5, Line 43 through Col. 7, Line 62 and Ex. 8, 12, 15, 39, 41, 52, 53, 58, 132, 138–140, 162–164, 166, 167, 169–182.

H. Gysin and E. Knusli, U.S. Pat. No. 2,891,855, June 23, 1959, Col. 3, Line 66 through Col. 5, Line 17 and Examples 1-4.

G. C. Klingman, "Weed Control as a Science", John Wiley & Sons, Inc., New York, 1961, pp. 81-96.

J. D. Fryer and S. A. Evans, "Weed Control Handbook", 5th Edn. Blackwell Scientific Publications, Oxford, 1968, pp. 101-103.

EXAMPLE 5

| Wettable Powder | |
|---|---|
| 2-(4-chlorophenyl)-2,3,5,6,7,8-hexahydro-3-thioxoimidazo[1,5-a]pyridin-1(8aH)-one | 40% |
| dioctyl sodium sulfosuccinate | 1.5% |
| sodium ligninsulfonate | 3% |
| low viscosity methyl cellulose | 1.5% |
| attapulgite | 54% |

The ingredients are thoroughly blended, passed through an air mill, to produce an average particle size under 15 microns, reblended, and sifted through a U.S.S. No. 50 sieve (0.3 mm. opening) before packaging.

All compounds of the invention may be formulated in the same manner.

EXAMPLE 6

| Aqueous Suspension | |
|---|---|
| 2-(4-chlorophenyl)-2,3,5,6,7,8-hexahydro-3-thioxoimidazo[1,5-a]pyridin-1(8aH)-one | 25% |
| hydrated attapulgite | 3% |
| crude calcium ligninsulfonate | 10% |
| sodium dihydrogen phosphate | 0.5% |
| water | 61.5% |

The ingredients are ground together in a ball or roller mill until the solid particles have been reduced to diameters under 10 microns.

EXAMPLE 7

| Solution and Granules | |
|---|---|
| 2-(4-chloro-2-fluorophenyl)-2,3,5,6,7,8-hexahydro-3-thioxoimidazo[1,5-a]pyridin-1(8aH)-one | 25% |
| dichloromethane | 75% |

The ingredients are combined and stirred to produce a solution. This solution is then sprayed onto preformed montmorillonoid clay granules (0.6-2.5 mm. in diameter) tumbling in a rotating drum. The rate of spray is adjusted to produce a 5% active granule after the dichloromethane is removed by evaporation. These granules are then packaged and are ready for use.

EXAMPLE 8

| Oil Suspension | |
|---|---|
| 2-(4-chlorophenyl)-2,3,5,6,7,8-hexahydro-3-thioxoimidazo[1,5-a]pyridin-1(8aH)-one | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 9

| High Strength Concentrate | |
|---|---|
| 2-(4-chlorophenyl)-2,3,5,6,7,8-hexahydro-3-thioxoimidazo[1,5-a]pyridin-1(8aH)-one | 98.5% |
| silica aerogel | 0.5% |
| synthetic amorphous fine silica | 1.0% |

The ingredients are blended and ground in a hammer mill to produce a high strength concentrate substantially all (e.g. 75%) passing a U.S.S. No. 50 sieve (0.3 mm openings). This material may then be formulated in a variety of ways known to those skilled in the art.

EXAMPLE 10

| Dust | |
|---|---|
| high strength concentrate, Example 9 (above) | 25.4% |
| pyrophyllite, powdered | 74.6% |

The materials are thoroughly blended and packaged for use.

UTILITY

The compounds of Formula I are useful for the selective preemergence weed control of undesired vegetation in crops such as rice, soybeans, peanuts, lima beans, green beans and squash. The compounds of this invention, can also be used as directed treatments for the pre/post-emergence control of weeds in various crops including soybeans, peanuts, garden beans and row-planted rice. In addition, these compounds are useful wherever general weed control is required, such as industrial sites, railroad and utility rights-of-way, along fences, building foundations, parking and storage lots, etc.

The amount of the compounds of Formula I to be used in any given situation will vary according to the particular end result desired, the use involved, the plant and soil involved, the formulation used, the mode of application, prevailing weather conditions, foliage density and like factors. Since so many variables play a role, it is not possible to state a rate of application suitable for all situations. Broadly speaking, the compounds of the invention are used at levels of about 0.125 to about 20 kilograms, preferably about 0.25 to 10, per hectare. The lower rates in this range will generally be selected on lighter soils, soils low in organic matter content, for selective weed control in crops, or in situations where maximum persistence is not necessary.

Herbicidal activity of compounds of this invention was determined in a greenhouse test.

TEST PROCEDURE

Seeds of crabgrass (Digitaria spp.), barnyardgrass (Echinochloa crusgalli), wild oats (Avena fatua), Cassia Tora, morningglory (Ipomoea spp.), cocklebur (Xanthium spp.) sorghum, corn, soybean, rice, wheat and nutsedge tubers were planted in a growth medium and treated preemergence with the chemicals dissolved in a non-phytotoxic solvent. At the same time, cotton having five leaves (including cotyledonary ones), bush beans with the third trifoliate leaf expanding, crabgrass with two leaves, barnyardgrass with two leaves, wild oats with one leaf, cassia with three leaves (including cotyledonary ones), morningglory with four leaves (including the cotyledonary ones), cocklebur with four leaves (including the cotyledonary ones), sorghum with three leaves, corn with three leaves, soybeans with two cotyledonary leaves, rice with two leaves, wheat with one leaf, and nutsedge with three-five leaves were sprayed. Treated plants and controls were maintained in a greenhouse for sixteen days, then all species were compared to controls and visually rated for response to treatment.

A quantitative rating was made on a scale of 0 to 10; a rating of 10 means complete kill, a rating of 0 means no injury. A qualitative rating for type of injury was also made; the letter "B" denotes foliage burn, "C" indicates chlorosis/necrosis and "H" stands for formative effects.

Ratings for one of the compounds tested by this procedure are recorded in the Table.

From the Table it is seen that the preferred compound of the instant invention has high herbicidal activity. Specifically, it is seen that in both pre- and post-emergence tests undesired vegetation such as morningglory is destroyed by the instant herbicides. It should be noted that the use of the instant herbicide as a preemergence herbicide results in particularly outstanding results. For instance, several different kinds of undesired vegetation e.g. crabgrass, wild oats, cassia, cocklebur, are effectively controlled by the instant herbicide.

TABLE

COMPOUND

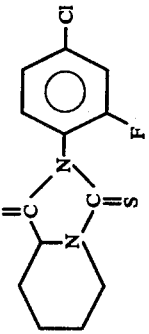

| kg./ha. | POST EMERGENCE | | | | | | | | | | | | | | PRE-EMERGENCE | | | | | | | | | | | |
|---|---|---|---|---|---|---|---|---|---|---|---|---|---|---|---|---|---|---|---|---|---|---|---|---|---|---|
| | Bush-bean | Cot-ton | Morn-ing glory | Cock-lebur | Cassia | Nuts-edge | Crab-grass | Barn-yard grass | Wild oats | Wheat | Corn | Soy-bean | Rice | Sorg-hum | Morn-ing glory | Cock-lebur | Cassia | Nuts-edge | Crab-grass | Barn-yard grass | Wild oats | Wheat | Corn | Soy-bean | Rice | Sorg-hum |
| 2 | 10B | 10B | 10B | 10B | 10B | 7B | 10B | 10B | 8B | 7B | 6B | 10B | 10B | 10B | 10E | 1C 6G | 10C | 3C | 7C | 10C | 9C | 9C | 2C 9H | 8H | 9C | 7C |

What is claimed is:

1. A method for the control of undesirable vegetation comprising applying to the locus of such undesired vegetation a herbicidally effective amount of a compound of the formula

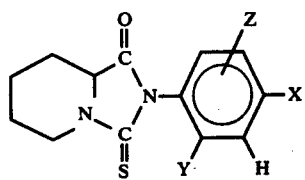

wherein

Z is hydrogen or fluorine;
Y is hydrogen or fluorine; and
X is bromine, chlorine, fluorine, methoxy, cyano, or nitro; provided that when Z is in the meta position and is fluorine, Y must also be fluorine.

2. A method for the control of undesirable vegetation comprising applying to the locus of such undesired vegetation a herbicidally effective amount of the compound of claim 1 wherein X is chlorine or fluorine; provided 1) that when X is fluorine at least one of Y or Z must be fluorine, 2) that when X is chlorine, at least one of Y or Z must be hydrogen and 3) that when Y and Z are both fluorine, X is also fluorine.